(12) United States Patent
Feinstein

(10) Patent No.: US 12,421,183 B2
(45) Date of Patent: Sep. 23, 2025

(54) METHANOL PRODUCTION METHOD

(71) Applicant: ZONEFLOW REACTOR TECHNOLOGIES, LLC, Windsor, CT (US)

(72) Inventor: Jonathan Jay Feinstein, Windsor, CT (US)

(73) Assignee: ZonePlow Reactor Technologies, LLC, Windsor, CT (US)

( * ) Notice: Subject to any disclaimer, the term of this patent is extended or adjusted under 35 U.S.C. 154(b) by 558 days.

(21) Appl. No.: 17/759,365

(22) PCT Filed: Jan. 22, 2021

(86) PCT No.: PCT/US2021/014691
§ 371 (c)(1),
(2) Date: Jul. 22, 2022

(87) PCT Pub. No.: WO2021/150942
PCT Pub. Date: Jul. 29, 2021

(65) Prior Publication Data
US 2023/0116003 A1 Apr. 13, 2023

Related U.S. Application Data

(60) Provisional application No. 62/965,637, filed on Jan. 24, 2020.

(51) Int. Cl.
*C07C 29/151* (2006.01)
*C01B 3/34* (2006.01)

(52) U.S. Cl.
CPC .......... *C07C 29/1518* (2013.01); *C01B 3/34* (2013.01); *C01B 2203/0233* (2013.01); *C01B 2203/061* (2013.01); *C01B 2203/0827* (2013.01); *C01B 2203/0894* (2013.01)

(58) Field of Classification Search
CPC ..... C07C 29/1518; C07C 31/04; C07C 29/78; C01B 3/34; C01B 2203/0233; C01B 2203/061; C01B 2203/0827; C01B 2203/0894; C01B 2203/0816; C01B 2203/1294; C01B 2203/84
See application file for complete search history.

(56) References Cited

U.S. PATENT DOCUMENTS

2016/0002035 A1\* 1/2016 Ralston ................. C01B 3/38
422/162

OTHER PUBLICATIONS

Kazumi et al (JP 04364142 A machine translation), Dec. 1992.\*
Masanobu et al (machine translation JP 09111268 A), Apr. 1997.\*

\* cited by examiner

*Primary Examiner* — Jafar F Parsa
(74) *Attorney, Agent, or Firm* — Knobbe, Martens, Olson & Bear LLP

(57) ABSTRACT

Syngas is produced by a steam reforming unit with at least one of a bayonet reactor for reforming steam and a hydrocarbon, a recuperative burner, and a regenerative burner such that the steam reforming unit produces little or no steam in excess of the steam reforming process requirements. The syngas is then converted to methanol in a methanol synthesis unit. Compressors for the synthesis unit are driven by higher efficiency drivers than are possible using the low temperature steam conventionally exported from a steam reforming unit.

19 Claims, 4 Drawing Sheets

METHANOL PRODUCTION METHOD

CROSS-REFERENCE TO RELATED APPLICATIONS

This application is the U.S. National Phase of International Application No. PCT/US2021/014691, filed Jan. 22, 2021, titled "METHANOL PRODUCTION METHOD," which claims the benefit of U.S. Provisional Application Ser. No. 62/965,637, filed Jan. 24, 2020, titled "METHANOL PRODUCTION METHOD," both of which are incorporated by reference herein in their entirety.

FIELD

The present disclosure relates to systems and methods for methanol production, and more particularly to systems and methods including a steam reforming unit and a methanol synthesis unit.

SUMMARY

In a first aspect, a method of producing methanol within a combination of a steam reforming unit and a methanol synthesis unit is described. The method comprises reforming, in a bayonet reforming reactor tube of the steam reforming unit, reactants comprising steam and a hydrocarbon to produce a reformate syngas at a first temperature; cooling the reformate syngas within the bayonet reforming reactor tube to a second temperature less than the first temperature; compressing the reformate syngas in at least one compressor of the methanol synthesis unit, the at least one compressor driven by a driver; and processing the compressed reformate syngas in a methanol synthesis reactor of the methanol synthesis unit to form a gas comprising steam and methanol.

In some embodiments, the driver comprises a gas turbine, a steam turbine utilizing inlet steam at a temperature greater than 550° C., a combination of a natural gas turbine and steam turbine, or an electric motor. In some embodiments, the driver is not driven by steam raised in the steam reforming unit. In some embodiments, the first temperature is at least 850° C. In some embodiments, the second temperature is less than 600° C. In some embodiments, the reactants comprise the steam and the hydrocarbon at a ratio of steam molecules to carbon atoms less than 3.0. In some embodiments, at least 70% of steam raised in the steam reforming unit is consumed in the steam reforming unit to reform the reactants. In some embodiments, the method further comprises generating the steam by heating feed water in at least a first heat exchanger configured to transfer heat from a furnace that heats the bayonet reforming reactor tube and a second heat exchanger configured to transfer heat from the reformate syngas. In some embodiments, the method further comprises cooling the gas comprising steam and methanol to yield liquid water containing methanol and a hydrocarbon gas. In some embodiments, the method further comprises recirculating at least a portion of the hydrocarbon gas as a fuel to a burner of the steam reforming unit.

In a second aspect, a method of producing methanol within a combination of a steam reforming unit and a methanol synthesis unit is described. The method comprises reforming, in a steam reforming furnace of the steam reforming unit, reactants comprising steam and a hydrocarbon to produce a reformate syngas, wherein the steam reforming furnace is heated by a regenerative burner or a recuperative burner; compressing the syngas in at least one compressor of the methanol synthesis unit, the at least one compressor driven by a driver; and processing the compressed reformate syngas in a methanol synthesis reactor of the methanol synthesis unit to form a gas comprising steam and methanol.

In some embodiments, the driver comprises a gas turbine, a steam turbine utilizing inlet steam at a temperature greater than 550° C., a combination of a natural gas turbine and steam turbine, or an electric motor. In some embodiments, the driver is not driven by steam raised in the steam reforming unit. In some embodiments, the reactants comprise the steam and the hydrocarbon at a ratio of steam molecules to carbon atoms less than 3.0. In some embodiments, at least 70% of steam raised in the steam reforming unit is consumed in the steam reforming unit to reform the reactants. In some embodiments, the method further comprises generating the steam by heating feed water in at least a first heat exchanger configured to transfer heat from a furnace that heats the bayonet reforming reactor tube and a second heat exchanger configured to transfer heat from the reformate syngas. In some embodiments, the method further comprises cooling the gas comprising steam and methanol to yield liquid water containing methanol and a hydrocarbon gas. In some embodiments, the method further comprises recirculating at least a portion of the hydrocarbon gas as a fuel to a burner of the steam reforming unit. In some embodiments, the regenerative burner or the recuperative burner is configured to preheat combustion air against combustion products of the regenerative burner or of the recuperative burner. In some embodiments, the combustion air is preheated to a temperature greater than 500° C.

DETAILED DESCRIPTION

Figure 1:
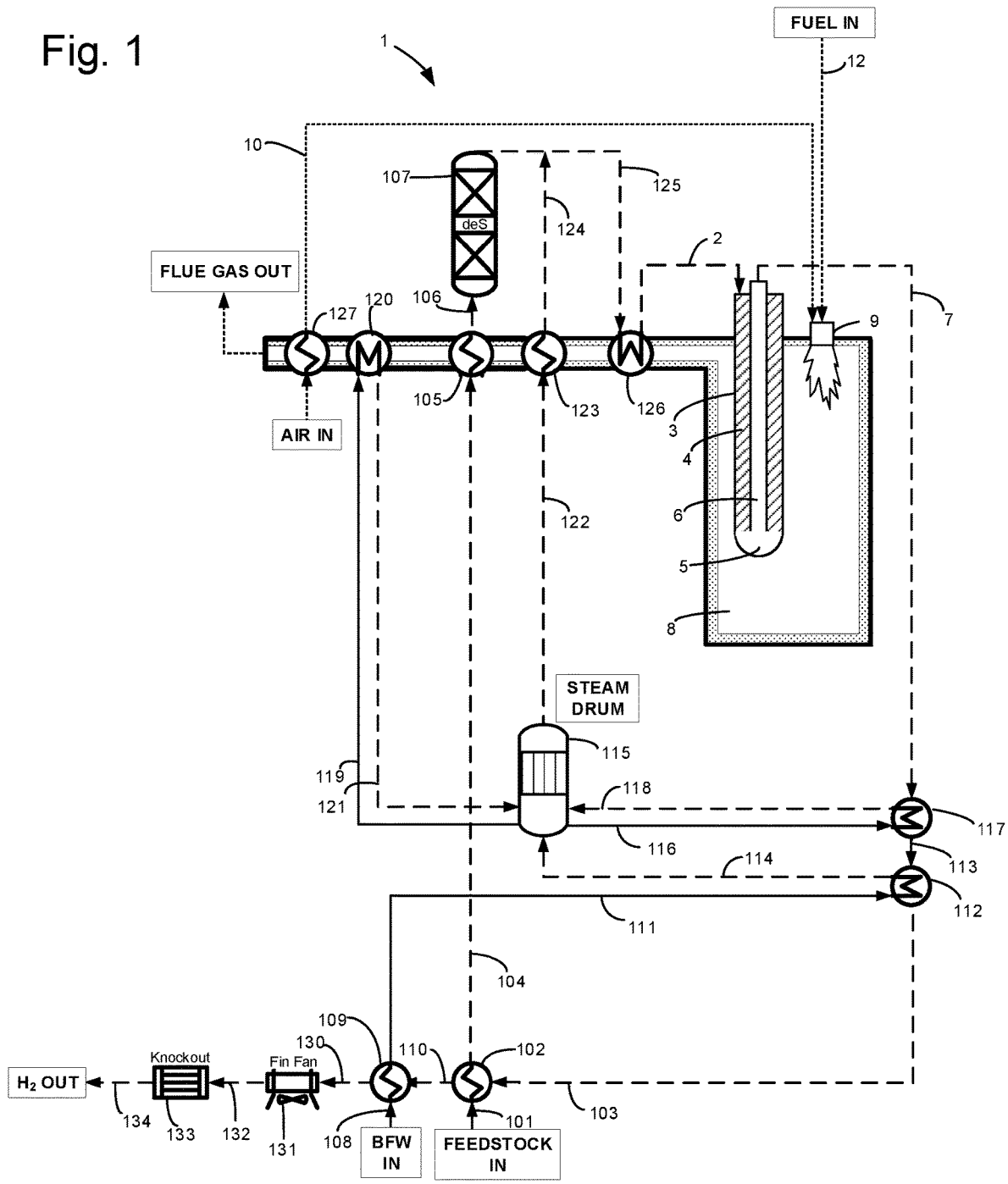
FIG. 1 shows a schematic of a hydrogen production unit of the present technology according to one embodiment.

Methanol is commonly produced via the steam reforming process to produce a syngas combined with additional carbon monoxide to produce a mixture containing about 2.25 moles of hydrogen to one mole of carbon monoxide. This syngas can be compressed and synthesized into methanol. The synthesis process consumes energy for compression of syngas from the steam reforming unit and for the recompression of recycle gas from the synthesis loop to a pressure of typically 150 to 300 bar-a for processing in a catalytic methanol synthesis unit. Energy efficiency of methanol production can be improved via reductions in the compression energy needed, for example, by lowering the pressure losses in the methanol synthesis unit or performing the synthesis at lower pressures.

Conventional steam reforming produces copious quantities of steam—in excess of the steam reforming requirements. Being otherwise unneeded, the excess or export steam is normally utilized to drive compressors for the synthesis unit. Although this usage of steam is seen as synergistic, the steam exported from the steam reforming unit, also referred to herein as the hydrogen production unit, is poorly suited for use in a steam turbine. In the steam reforming unit, steam is generated in the recoveries of heat from syngas and from the combustion gases exiting the reformer. Because the syngas must be cooled quickly, normally against boiler feed water, to temperatures below those at which the syngas is corrosive to the equipment and thereby minimize such corrosion, the steam cannot conventionally be heated to temperatures above the range of 500° to 550° C. Even at elevated pressure, steam of this quality provides only about 30% thermal efficiency when used in a steam turbine. By comparison, hotter steam, a gas turbine, or a combined cycle of natural gas and steam turbines could reach thermal efficiencies of up to 60%. To take advantage of higher thermal efficiencies for driving compressors without forfeiting the energy value of excess steam from reforming, it is necessary to either utilize the excess steam in another, more effective way or reduce the amount of excess low-quality steam created by the reformer. Accordingly, in some embodiments of the present technology, a methanol synthesis unit includes compressors driven by drivers that are not driven by steam raised in an associated steam reforming unit.

Bayonet reactors may be used for steam reforming. They consist of two concentric tubes. The outer tube is open at a first end and blocked at a second end. A mixed feed of steam and hydrocarbons is introduced into an annulus between the tubes at the first end, flows to the second end of the tube through a catalytic reactor in the annulus, traverses at the second end to the inner tube through which the reformed syngas flows back to the first end and exits the bayonet tube. The heat of reaction is provided by both the furnace outside the outer tube and from the heat recovered from the return gas in the inner tube.

Regenerative and recuperative burners may be used for a variety of heating applications, but are not typically used or known to be economical or useful for methanol production via steam reforming followed by a methanol synthesis process for the novel purposes identified in the present disclosure.

Certain embodiments of the present disclosure at least partially replace the conventional use of excess steam from a steam reforming unit with a more energy efficient resource such as a gas turbine or a natural gas turbine combined with a steam turbine to drive compressors used in methanol production. Some embodiments advantageously reduce the steam consumption of the steam reformer used for methanol production. Moreover, some embodiments reduce or eliminate the heat exchanger requirements for raising steam from the flue gases and from the hot syngas of the steam reformer. Other advantages of the present technology will be observed by one skilled in the art.

In accordance with the present technology, a mixed feed of steam and one or more hydrocarbons can be reformed to produce a syngas containing hydrogen and oxides of carbon in a bayonet catalytic reactor. The feed may also contain carbon dioxide or carbon monoxide. Reforming is preferably performed to a peak temperature of at least 850° C. and more preferably at least 900° C. Reforming is preferably performed at a ratio of steam molecules to carbon atoms in the mixed feed (S/C ratio) less than 3.0 and more preferably less than 2.6. The reformed and cooled syngas preferably exits the inner tube of the bayonet reactor at a temperature less than 880° C., more preferably less than 600° C., and most preferably at a temperature less than 500° C. in some embodiments, the reforming catalytic reactor can advantageously be a structured packing.

Heat is transmitted to the reforming reactor from a heater. In some embodiments, the heater is a combustion fired furnace. In some embodiments, the furnace is fired by at least one of a recuperative and a regenerative burner, and in some embodiments, by recuperative burners. Recuperative burners perform the combustion air preheat function of the convective zone of conventional reformers and can replace at least some of the functions of the convective zone of recovering heat from the combustion products to preheat boiler feed water, feedstock, and mixed feed and to raise and superheat steam. Recuperative and regenerative burners recover heat from the combustion products mainly to preheat the combustion air, thereby reducing the amount of fuel needed for heating and the amount of heat contained in the combustion products exiting the radiant zone of the furnace from which to recover heat. Regenerative and recuperative burners are distinguished from the combustion air preheat sections of conventional convective zones in steam reforming units in at least one of two ways. The first way is that regenerative and recuperative burners may preheat combustion air to temperatures in excess of 500° C. and up to about 1100° C., whereas the air preheat sections of conventional convective zones in steam reforming units typically heat air to no more than 250-400° C. The second way is that air preheating is performed at multiple locations within or near multiple individual burners as opposed in a central convective section as is conventional in steam reforming. Systems distinguished in at least one of these two ways are defined herein as systems with recuperative or regenerative burners. Recuperative burners are distinguished from regenerative burners in that recuperative burners utilize indirect heat transfer between combustion products and combustion air, and regenerative burners utilize direct heat transfer to and from a heat storage mass or checkers.

Because the thermal mass of the combustion products is greater than that of the combustion air alone, recuperative and regenerative burners could be advantageously used for heating needs additional to preheating the combustion air. Example uses include boiler feed water preheating, steam raising, steam superheating, feedstock preheating, and mixed feed preheating.

The bayonet reactor provides numerous benefits, particularly for methanol production. By cooling the reformed syngas against inlet process gas to the bayonet reactor, heat is recovered to produce hydrogen rather than to produce excess low value steam.

Secondly, single pass reforming reactor tubes can be constrained by the outlet system metallurgy to an outlet temperature of no more than about 880° C. Bayonet reactors can reform to peak reforming temperatures in excess of 900° C. with existing reformer tube metallurgy and then cool the syngas below 880° C. before the gas enters the outlet system.

Lastly, it can be advantageous to lower the energy requirements of the steam reformer by lowering the steam-to-carbon (S/C) ratio as much as possible. At lower S/C ratios, more methane remains unconverted. By reforming to higher peak temperatures than are possible in single pass reactors, bayonet reforming reactors reform more methane to hydrogen and accommodate lower S/C ratios without leaving excessive amounts of unreacted methane in the syngas. The lower S/C ratios possible with bayonet reactors lower the energy consumption of the steam reformer. Syngas with less residual steam content also requires less heat exchanger surface area for the condensation of steam which is necessary in the cooling of the syngas.

The multiple compressors for compressing makeup and recycle process gas for methane synthesis are driven by means selected from the group of a steam turbine using inlet steam that is hotter than 550° C., a gas turbine, a combined cycle gas turbine and steam turbine unit, an electric motor, and any device generating power at lower cost than using the steam from a steam reforming unit. Use of the more efficient means of driving compressors results from the specific means by which the present art reduces steam export.

At least 70%, preferably at least 80% and more preferably at least 90% of the steam raised in the hydrogen production unit is consumed in the hydrogen production unit.

FIG. 1 depicts an example embodiment of a hydrogen production unit 1.

A mixed feed is conveyed via line 2 to bayonet reformer tube 3, entering the annulus 4, flowing to the tip 5, and returning via inner tube 6. The mixed feed is both heated and converted to syngas containing hydrogen in the annulus which contains a catalyst, reaching a first temperature at the tip and a second temperature lower than the first temperature at the outlet and outlet line 7.

The reformer tube is at least partially disposed within a reformer furnace 8. A burner 9 heats the furnace, being supplied with air via line 10, and fuel via line 12.

Line 101 conveys a hydrocarbon feedstock to heat exchanger 102 wherein the feedstock is preheated against syngas from line 103. The preheated feedstock is conveyed by line 104 from heat exchanger 102 to heat exchanger 105 wherein it is further heated against combustion products from the furnace to a temperature suitable for desulphurization. Line 106 conveys the further heated feedstock from heat exchanger 105 to desulphurization unit 107 wherein the feedstock is desulphurized.

Boiler feed water is conveyed via line 108 to heat exchanger 109 wherein it is heated against syngas from line 110. The heated boiler feed water is conveyed via line 111 from heat exchanger 109 to heat exchanger 112 wherein it is vaporized to steam against syngas from line 113. The resultant steam is conveyed by line 114 from heat exchanger 112 to steam drum 115. The steam drum distributes liquid phase water via line 116 to heat exchanger 117 wherein it is vaporized against syngas from line 7 and whereupon the resultant steam is returned from heat exchanger 117 via line 118 to the steam drum. The steam drum also distributes liquid phase water via line 119 to heat exchanger 120 wherein it is vaporized against combustion products from the furnace and whereupon the resultant steam is returned from heat exchanger 120 via line 121 to the steam drum.

Steam is conveyed from the steam drum via line 122 to heat exchanger 123 wherein it is superheated against combustion products from the furnace. The superheated steam is conveyed via line 124 from heat exchanger 123 to line 125 wherein the superheated steam mixes with the feedstock exiting the desulphurization unit 107 via line 125. Line 125 further conveys the mixed feed to heat exchanger 126 wherein the mixed feed is preheated against combustion products from the furnace. The preheated mixed feed is conveyed via line 2 from heat exchanger 126 to the bayonet reformer tube.

Ambient air is inducted into heat exchanger 127 wherein it is preheated against combustion products from the furnace. The preheated air is conveyed via line 10 from heat exchanger 127 to the burner wherein it combusts with fuel to heat the furnace.

The syngas exiting the reformer via line 7 is sequentially cooled in heat exchanger 117, conveyed via line 113 to heat exchanger 112 wherein it is further cooled, conveyed via line 103 to heat exchanger 102 wherein it is cooled against feedstock, conveyed via line 110 to heat exchanger 109 wherein it is cooled against boiler feed water, conveyed via line 130 to fin fan heat exchanger 131 wherein it is cooled against ambient air and some of the steam content of the syngas condenses, conveyed via line 132 to water knockout unit 133 wherein condensed water is removed from the syngas, and conveyed via line 134 to a methanol synthesis unit.

Upon combustion in the furnace, the products of combustion sequentially pass through heat exchangers 126, 123, 105, 120, and 127 and finally exit the hydrogen production unit.

The numerals in the figures correspond to equivalent components of the various figures.

Figure 2:
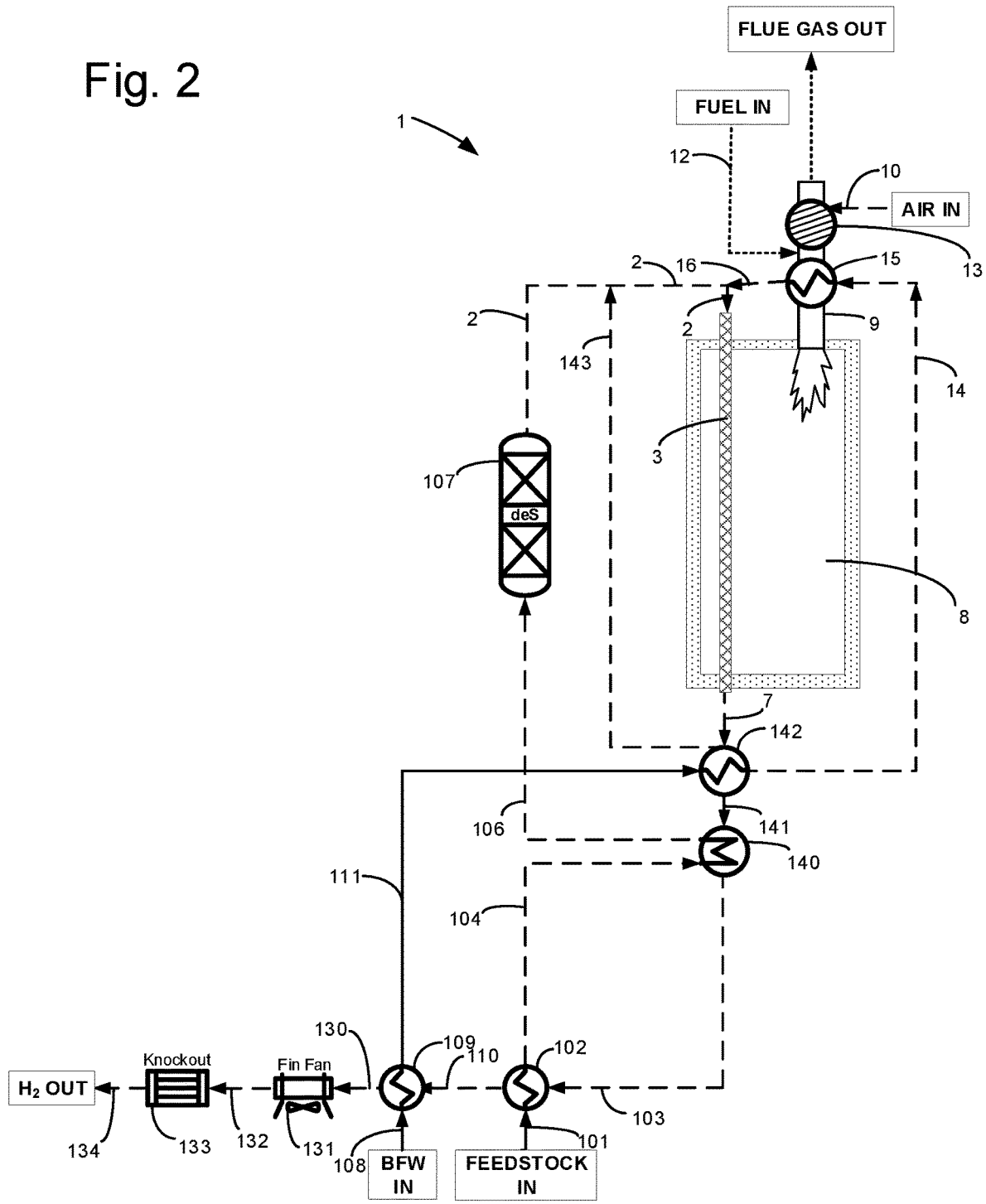
FIG. 2 shows a schematic of a hydrogen production unit of the present technology according to another embodiment.

FIG. 2 illustrates another example embodiment of a hydrogen production unit 1. A mixed feed is conveyed via line 2 to single pass reformer tube 3 containing a suitable catalyst wherein the mixed feed is both heated and converted to a syngas containing hydrogen. Syngas exits the tube via outlet line 7.

The reformer tube is at least partially disposed within reformer furnace 8. Recuperative or regenerative burners 9 heat the furnace, being supplied with air via line 10 and fuel via line 12. The inducted air is preheated in heat exchanger 13 within the burner against products of combustion from the furnace before the air is combusted with fuel.

Preferably, steam line 14 conveys steam to heat exchanger 15 preferably within the burner wherein the steam is superheated against combustion products from the furnace. The superheated steam is conveyed via line 16 to line 2 wherein the steam mixes with mixed feed and is conveyed into the reformer tube.

Line 101 conveys a hydrocarbon feedstock to heat exchanger 102 wherein the feedstock is preheated against syngas from line 103. The preheated feedstock is conveyed by line 104 from heat exchanger 102 to heat exchanger 140 wherein it is further heated against syngas from line 141 to a temperature suitable for desulphurization. Line 106 conveys the further heated feedstock from heat exchanger 140 to desulphurization unit 107 wherein the feedstock is desulphurized.

Boiler feed water is conveyed via line 108 to heat exchanger 109 wherein it is heated against syngas from line 110. The heated boiler feed water is conveyed via line 111 from heat exchanger 109 to heat exchanger 142 wherein the water is vaporized to steam against syngas from line 7. The resultant steam is conveyed by line 143 from heat exchanger 142 to line 2 wherein the superheated steam mixes with the feedstock exiting the desulphurization unit via line 2. The resultant mixed feed is conveyed via line 2 to the single pass reformer tube.

The syngas exiting the reformer via line 7 is sequentially cooled in heat exchanger 142, conveyed via line 141 to heat exchanger 140 wherein it is further cooled, conveyed via line 103 to heat exchanger 102 wherein it is cooled, conveyed via line 110 to heat exchanger 109 wherein it is cooled, conveyed via line 130 to fin fan heat exchanger 131 wherein it is cooled against ambient air and some of the steam content of the syngas condenses, conveyed via line 132 to water knockout unit 133 wherein condensed water is removed from the syngas, and conveyed via line 134 from the knockout unit to a methanol synthesis unit.

Line 14 conveys a second stream of steam from heat exchanger 142 to heat exchanger 15.

Upon exiting the furnace, the products of combustion sequentially pass through heat exchangers 15 and 13 wherein they are cooled and finally exit the hydrogen production unit 1.

Figure 3:
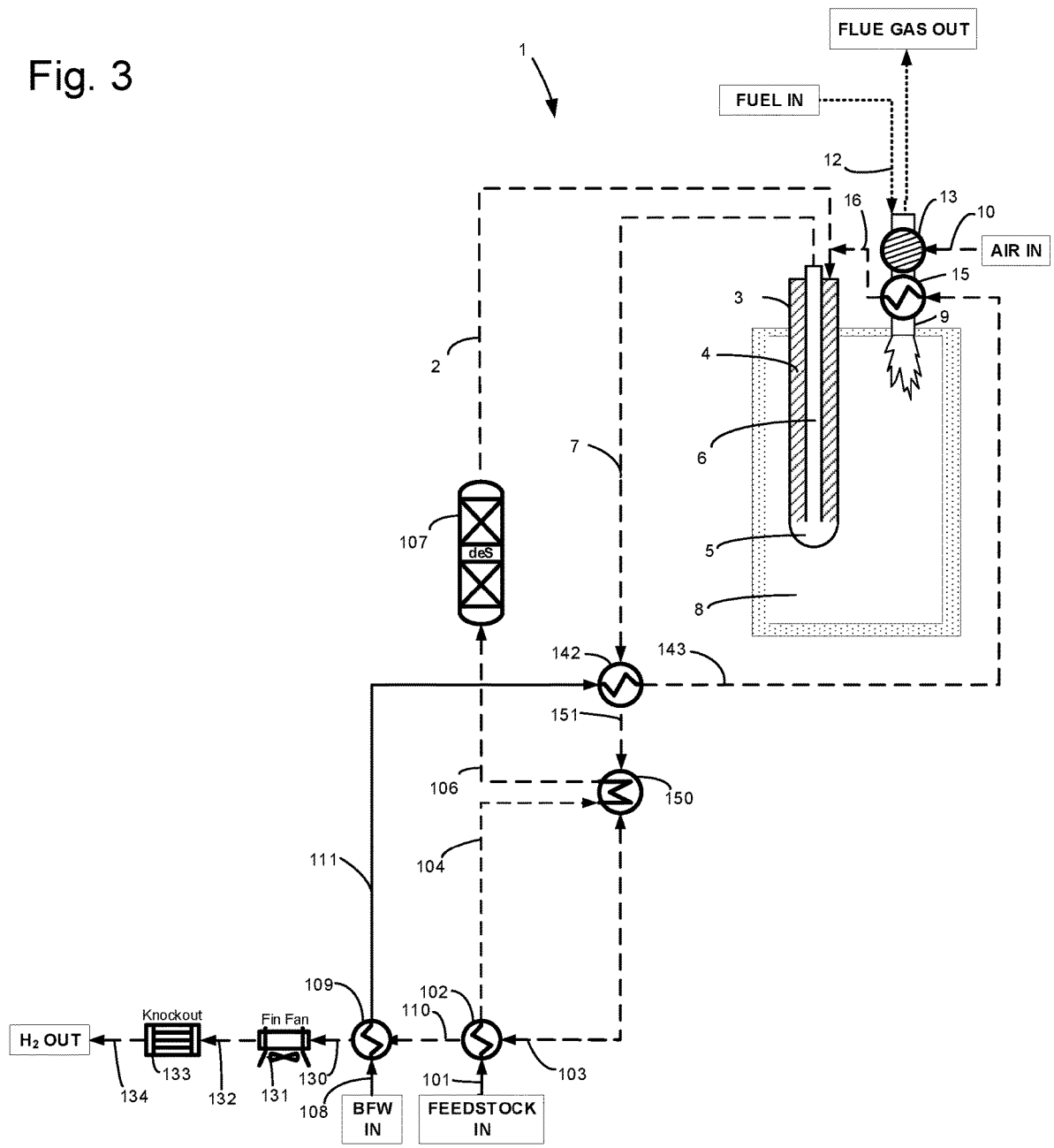
FIG. 3 shows a schematic of a hydrogen production unit of the present technology according to another embodiment.

FIG. 3 depicts an example embodiment of a hydrogen production unit 1. A mixed feed is conveyed via line 2 to bayonet reformer tube 3, entering the annulus 4, flowing to the tip 5, and returning via inner tube 6. The mixed feed is both heated and converted to syngas containing hydrogen in the annulus which contains a catalyst, reaching a first temperature at the tip and a second temperature lower than the first temperature at the outlet and outlet line 7.

The reformer tube is at least partially disposed within reformer furnace 8. Recuperative burner 9 heats the furnace, being supplied with air via line 10 and fuel via line 12. The inducted air is preheated in heat exchanger 13 within the regenerative burner against products of combustion from the furnace before the air is combusted with fuel.

Line 101 conveys a hydrocarbon feedstock to heat exchanger 102 wherein the feedstock is preheated against syngas from line 103. The preheated feedstock is conveyed by line 104 from heat exchanger 102 to heat exchanger 150 wherein it is further heated against syngas from line 151 to a temperature suitable for desulphurization. Line 106 conveys the further heated feedstock from heat exchanger 150 to desulphurization unit 107 wherein the feedstock is desulphurized.

Boiler feed water is conveyed via line 108 to heat exchanger 109 wherein it is heated against syngas from line 110. The heated boiler feed water is conveyed via line 111 from heat exchanger 109 to heat exchanger 142 wherein the water is vaporized to steam against syngas from line 7. The resultant steam is conveyed by line 143 from heat exchanger 142 to heat exchanger 15 within the burner wherein the steam is superheated against combustion products from the furnace. The superheated steam is conveyed via line 16 from heat exchanger 15 to line 2 wherein the superheated steam mixes with the feedstock exiting the desulphurization unit via line 2. The resultant mixed feed is conveyed via line 2 to the bayonet reformer tube.

The syngas exiting the reformer via line 7 is sequentially cooled in heat exchanger 142, conveyed via line 151 to heat exchanger 150 wherein it is further cooled, conveyed via line 103 to heat exchanger 102 wherein it is cooled, conveyed via line 110 to heat exchanger 109 wherein it is cooled, conveyed via line 130 to fin fan heat exchanger 131 wherein it is cooled against ambient air and some of the steam content of the syngas condenses, conveyed via line 132 to water knockout unit 133 wherein condensed water is removed from the syngas, and conveyed via line 134 to a methanol synthesis unit.

Upon combustion in the furnace, the products of combustion sequentially pass through heat exchangers 15 and 13 wherein they are cooled and finally exit the hydrogen production unit.

Figure 4:
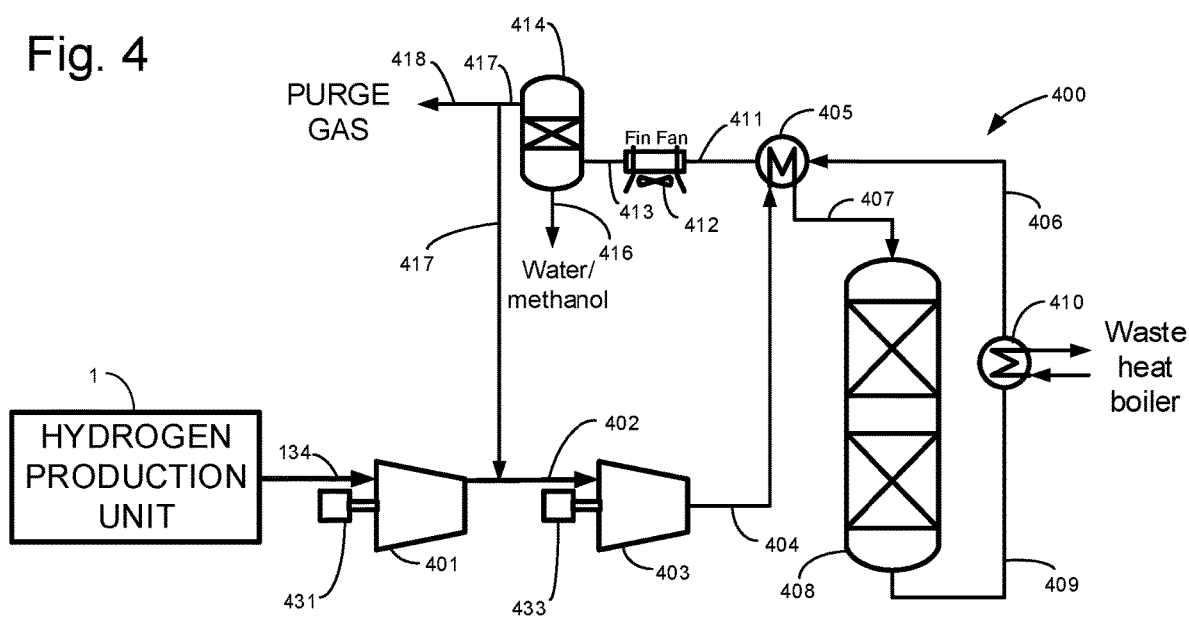
FIG. 4 shows a schematic of a hydrogen production unit in combination with a methanol synthesis unit of the present technology according to one embodiment.

FIG. 4 depicts a methanol production unit 400 consists of a combination of a steam reforming hydrogen production unit 1 and a methanol synthesis unit. Syngas containing hydrogen and carbon monoxide is supplied by line 134 from the steam reforming hydrogen production unit 1 and a methanol synthesis unit. The hydrogen production unit 1 may be any of the units 1 shown in FIG. 1, 2, or 3.

Syngas is conveyed via line 134 from hydrogen production unit 1 to compressor 401 wherein the syngas is compressed. The syngas is conveyed by line 402 from compressor 401 to compressor 403 wherein the syngas along with recirculated gas from line 417 is compressed to a pressure suitable for methanol synthesis, such as 150 to 250 bar-g for example. The fully compressed gas is conveyed via line 404 from compressor 403 to heat exchanger 405 wherein the compressed gas is heated against methanol bearing gas from line 406. The heated gas is conveyed via line 407 from heat exchanger 405 to methanol synthesis reactor 408 wherein it is exposed to a suitable catalyst and exothermically reacts to a steam of higher methanol concentration. The reacted gas is conveyed via line 409 from the reactor to waste heat boiler 410 wherein it is cooled against boiler feed water, resulting in the boiler feed water being vaporized to steam. The cooled reacted gas is conveyed via line 406 from boiler 410 to heat exchanger 405 wherein it is further cooled against gas from line 404. The further cooled gas is conveyed via line 411 from heat exchanger 405 to heat exchanger 412 wherein it is cooled against ambient air, some steam condenses, and some methanol dissolves in the steam condensate. The resultant gas and liquid are conveyed via line 413 from unit 412 to phase separator 414 wherein the liquid and gas phases are separated. Liquid water containing methanol exits the separator via line 416, and some of the remaining gas is recirculated via line 417 from the phase separator 414 to line 402 and then to compressor 403 wherein the recirculated gas is repressurized for recirculation to the methanol synthesis reactor. A portion of the gas in line 417 is metered and purged to line 418 for use as fuel in the furnace of the hydrogen production unit. The gas in line 418 is conveyed to burners in the steam reforming unit (shown in FIGS. 1, 2, and 3) wherein the gas is combusted as fuel.

Compressor 401 is driven by driver 431, and compressor 403 is driven by driver 433. At least one of drivers 431 and 433 is at least one of a gas turbine, a steam turbine utilizing inlet steam at a temperature greater than 550° C. and more preferably greater than 600°, and most preferably greater than 650° C., a combined cycle gas turbine and steam turbine, and an electric motor.

Although the present technology has been described in terms of certain preferred embodiments, various features of separate embodiments can be combined to form additional embodiments not expressly described. Moreover, other embodiments apparent to those of ordinary skill in the art after reading this disclosure are also within the scope of this technology. Furthermore, not all the features, aspects and advantages are necessarily required to practice the present technology. Thus, while the above detailed description has shown, described, and pointed out novel features of the technology as applied to various embodiments, it will be understood that various omissions, substitutions, and changes in the form and details of the apparatus or process illustrated may be made by those of ordinary skill in the technology without departing from the spirit or scope of the present disclosure. The technology may be embodied in other specific forms not explicitly described herein. The embodiments described above are to be considered in all respects as illustrative only and not restrictive in any manner.

What is claimed is:

1. A method of producing methanol within a combination of a steam reforming unit and a methanol synthesis unit, the method comprising:

reforming, in a bayonet reforming reactor of the steam reforming unit, reactants comprising steam and a hydrocarbon to produce a reformate syngas at a first temperature, wherein the first temperature is at least 850° C.;

cooling the reformate syngas within the bayonet reforming reactor tube to a second temperature less than the first temperature;

compressing the reformate syngas in at least one compressor of the methanol synthesis unit, the at least one compressor driven by a driver; and processing the compressed reformate syngas in a methanol synthesis reactor of the methanol synthesis unit to form a gas comprising steam and methanol.

2. The method of claim 1, wherein the driver comprises a gas turbine, a steam turbine utilizing inlet steam at a temperature greater than 550° C., a combination of a natural gas turbine and steam turbine, or an electric motor.

3. The method of claim 1, wherein the driver is not driven by steam raised in the steam reforming unit.

4. The method of claim 1, wherein the second temperature is less than 600° C.

5. The method of claim 1, wherein the reactants comprise the steam and the hydrocarbon at a ratio of steam molecules to carbon atoms less than 3.0.

6. The method of claim 1, wherein at least 70% of steam raised in the steam reforming unit is consumed in the steam reforming unit to reform the reactants.

7. The method of claim 1, further comprising generating the steam by heating feed water in at least a first heat exchanger configured to transfer heat from a furnace that heats the bayonet reforming reactor tube and a second heat exchanger configured to transfer heat from the reformate syngas.

8. The method of claim 1, further comprising cooling the gas comprising steam and methanol to yield liquid water containing methanol and a hydrocarbon gas.

9. The method of claim 8, further comprising recirculating at least a portion of the hydrocarbon gas as a fuel to a burner of the steam reforming unit.

10. A method of producing methanol within a combination of a steam reforming unit and a methanol synthesis unit, the method comprising:
  reforming, in a steam reforming furnace of the steam reforming unit, reactants comprising steam and a hydrocarbon to produce a reformate syngas, wherein the steam reforming furnace is heated by a regenerative burner or a recuperative burner, wherein the reformate syngas is produced at a peak reforming temperature of at least 850° C.;
  compressing the syngas in at least one compressor of the methanol synthesis unit, the at least one compressor driven by a driver; and
  processing the compressed reformate syngas in a methanol synthesis reactor of the methanol synthesis unit to form a gas comprising steam and methanol.

11. The method of claim 10, wherein the driver comprises a gas turbine, a steam turbine utilizing inlet steam at a temperature greater than 550° C., a combination of a natural gas turbine and steam turbine, or an electric motor.

12. The method of claim 10, wherein the driver is not driven by steam raised in the steam reforming unit.

13. The method of claim 10, wherein the reactants comprise the steam and the hydrocarbon at a ratio of steam molecules to carbon atoms less than 3.0.

14. The method of claim 10, wherein at least 70% of steam raised in the steam reforming unit is consumed in the steam reforming unit to reform the reactants.

15. The method of claim 10, further comprising generating the steam by heating feed water in at least a first heat exchanger configured to transfer heat from a furnace that heats the bayonet reforming reactor tube and a second heat exchanger configured to transfer heat from the reformate syngas.

16. The method of claim 10, further comprising cooling the gas comprising steam and methanol to yield liquid water containing methanol and a hydrocarbon gas.

17. The method of claim 16, further comprising recirculating at least a portion of the hydrocarbon gas as a fuel to a burner of the steam reforming unit.

18. The method of claim 10, wherein the regenerative burner or the recuperative burner is configured to preheat combustion air against combustion products of the regenerative burner or of the recuperative burner.

19. The method of claim 18, wherein the combustion air is preheated to a temperature greater than 500° C.

\* \* \* \* \*